United States Patent [19]

Swandic

[11] Patent Number: 5,760,388
[45] Date of Patent: Jun. 2, 1998

[54] BIOMEDICAL IMAGING BY OPTICAL PHASE CONJUGATION

[75] Inventor: James R. Swandic, Silver Spring, Md.

[73] Assignee: The United States of America as represented by the Secretary of the Navy, Washington, D.C.

[21] Appl. No.: 449,582

[22] Filed: May 24, 1995

[51] Int. Cl.$^6$ ........................................... A61B 1/06
[52] U.S. Cl. .................................. 250/221; 606/18
[58] Field of Search .................... 250/221, 201.9; 606/16, 17, 18, 15

[56] References Cited

U.S. PATENT DOCUMENTS 4,928,695  5/1990  Goldman et al. ............... 606/15
5,089,384  2/1992  Hale ............................. 250/461.2
5,125,417  6/1992  Nebenzahl ....................... 607/154

*Primary Examiner*—Edward P. Westin
*Assistant Examiner*—Kevin Pyo
*Attorney, Agent, or Firm*—John Forrest; Jacob Shuster

[57] ABSTRACT

Biological tissue is imaged by non-damaging illumination from a coherent light source and retroreflective radiation from a phase conjugate mirror without correction for absorption induced distortion. Optics is provided to regulate the illumination and to direct the retroreflective imaging radiation from the targeted biological tissue. Such imaging radiation is maintained substantially at unity reflectivity.

12 Claims, 4 Drawing Sheets

5,760,388

BIOMEDICAL IMAGING BY OPTICAL PHASE CONJUGATION

BACKGROUND OF THE INVENTION

The present invention relates generally to the imaging of biological targets by non-invasive optical illumination methods for diagnostic and/or research purposes.

The application of electromagnetic radiation to biomedical imaging of a targeted medium has expanded from previous use of x-rays into illumination by radiation within the visible region of the spectrum. Where the targeted medium is human tissue, the scattering of illuminating lights predominates over its absorption by about two orders of magnitude so that multiple scattering effects heretofore overwhelmed acceptable imaging in the absence of corrective measures requiring high power levels, sensitive detectors, time gating, etc.

Independently of the use of visible radiation for biomedical imaging purposes, optical phase conjugation has been developed as a non-linear process to reverse the wavefront of incident radiation for return to its source. Under suitable circumstances, such optical phase conjugation process can correct distortions of incident radiation induced by a lossless scattering object. To be useful for non-invasive diagnostic imaging, various problems with phase conjugation as the basis for imaging must be dealt with. Such problems arise because of radiation absorption and multiple scattering by human tissue, to be suppressed, and to avoid tissue damage despite use of radiation of sufficient intensity for acceptable imaging exceeding the damage threshold.

It is therefore an important object of the present invention to provide non-invasive biomedical imaging of human tissue or the like for direct observation or detection by use of incident light radiation at safe power levels and without extensive computer manipulation of data on the scattered signal so obtained.

An additional object in accordance with the foregoing object is to provide biomedical imaging of acceptable quality despite use of illuminating light without damage to human tissue and image distortion induced by light absorption in such tissue, which forms the basis for such imaging.

SUMMARY OF THE INVENTION

In accordance with the present invention, monochromatic radiation of low variable intensity in the red or near infrared region is radiated from a source of coherent light through a target medium to a phase conjugate mirror within which the incident light is reflected by non-linear wavefront reversal onto the target medium. Such target medium to be imaged includes in-vivo biological tissue translucent to the incident light with little absorption, and has a multiple light scatter property predominating over light absorption to allow substantial penetration. A detection or therapeutic "window" within the red or near infrared spectral region of the incident light is thereby established.

The non-linear phase conjugation process aforementioned reverses the incident light wave front while repeated reflection of the light wave between the phase conjugate mirror and the target tissue suppresses the effects of multiple scattering in the target tissue to obtain acceptable imaging in arbitrary directions by maintaining reflectivity substantially at unity. Such phase conjugation is performed at room temperature by delivery of incident light to a phase conjugate mirror, continuously or during spaced intervals of time of greater duration than the typical time light would stay in the target tissue—phase conjugate mirror system. A steady state of light of sufficient duration is thereby established. Various optical measures are also introduced to insure good quality imaging by the mirror during the phase conjugation process without correction of absorption induced image distortion, as the basis for tissue imaging.

BRIEF DESCRIPTION OF DRAWING FIGURES

A more complete appreciation of the invention and many of its attendant advantages will be readily appreciated as the same becomes better understood by reference to the following detailed description when considered in connection with the accompany drawing wherein.

DETAILED DESCRIPTION OF PREFERRED EMBODIMENTS

Figure 1:
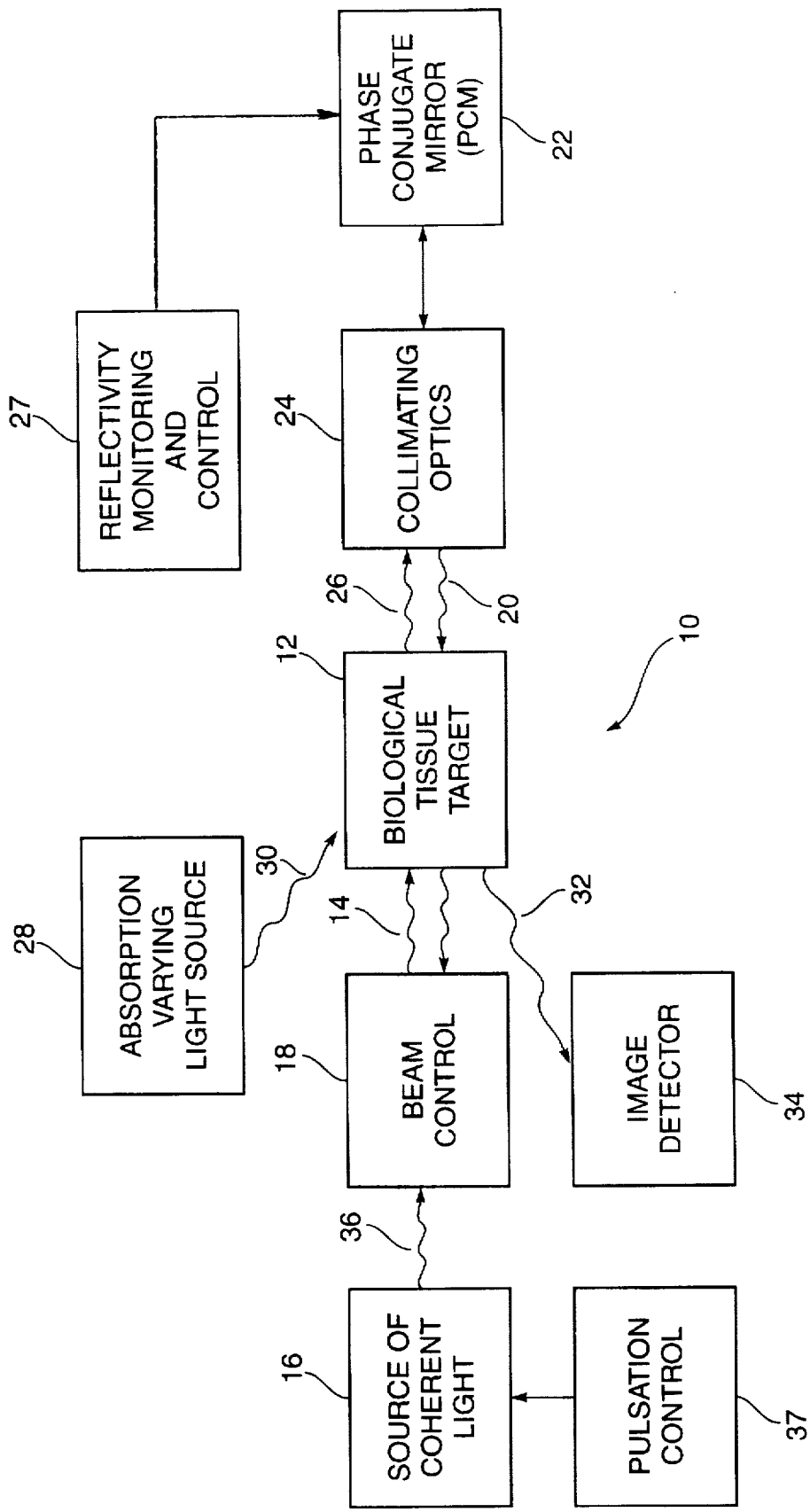
FIG. 1 is a block diagram of a biomedical imaging system in accordance with one embodiment of the invention.

Referring now to the drawing in detail, FIG. 1 diagrams a biological imaging system 10 in accordance with certain embodiments of the invention. As denoted by block 12 of the diagrammed system 10, a biological tissue sample as a target is illuminated on one side by a beam 14 derived from a coherent light source 16 through a beam control component 18. The opposite side of the biological tissue target 12 is illuminated by a beam 20 retroreflected from illumination 26 emerging from the target 12 and entering a phase conjugate mirror component 22 having collimating optics 24 in front thereof as diagrammed in FIG. 1. The light beams 20 and 26 are thus formed by multiple reflections of light between tissue target 12 and the phase conjugate mirror 22 in series with the collimating optics 24. While the phase conjugate mirror 22 is generally known in the art, certain constraints are associated therewith pursuant to the present invention so as to accommodate distortion induced by backscattering, as well as to meet other conditions imposed by predominance of multiple scattering and specific limits set by the biological tissues being examined as the target 12. While various known types of phase conjugate mirrors may be utilized, in all cases it is essential that its reflectivity (Rc) be maintained at unity under the conditions imposed by the present invention. Toward that end, the system 10 is provided with a reflectivity monitor and control component 27 as diagrammed in FIG. 1.

Also diagrammed in FIG. 1 is an optional radiation source 28 illuminating the target 12 to change the light absorption coefficient attributable to specific parts or features thereof. The additional light 30 from source 28 is incoherent with the light 14, 20 and 26 used for phase conjugate imaging and may have a different frequency. The source 28 is thus pulsed at a rate consonant with the response time of the phase conjugate mirror 22 so as to maximize detection of regions within the tissue target 12 by inducing absorption changes, with the phase conjugate mirror 22 acting as a filter to detect time variations for such changes in absorption.

With continued reference to FIG. 1, the collimating optics 24 in front of the phase conjugate mirror 22 collimates the light of illumination 26 scattered in all directions to the right by the tissue of target 12 so as to concentrate it onto an incident surface of the phase conjugate mirror 22, resulting in multiple reflections between the target and system of mirror and optics, and the emergence of imaging light 32 from the target 12 for reception by an image detector 34. The distance between the image detector 34 and target 12 is great enough to render evanescent modes negligible.

According to a most simple embodiment, the image detector 34 is the human eye protected by a filter to limit intensity below the damage threshold for imaging in the red or near infrared spectral range made visible to the eye by a fluorescent screen. The image can also be detected by a charge-coupled device (CCD) or video camera sensitive to such spectral region, and recorded electronically or on video tape. Since the image is carried on a coherent light beam, one can divert by a beamsplitter some of the incident light beam 14 coherent with it and record the image as a hologram on photographic film. The detector 34 is sensitive enough in the red or near infrared range to produce or record an image from light 32, weak enough not to damage the biological tissue target 12, and with a speed greater than any motion of the target 12.

Figure 2:
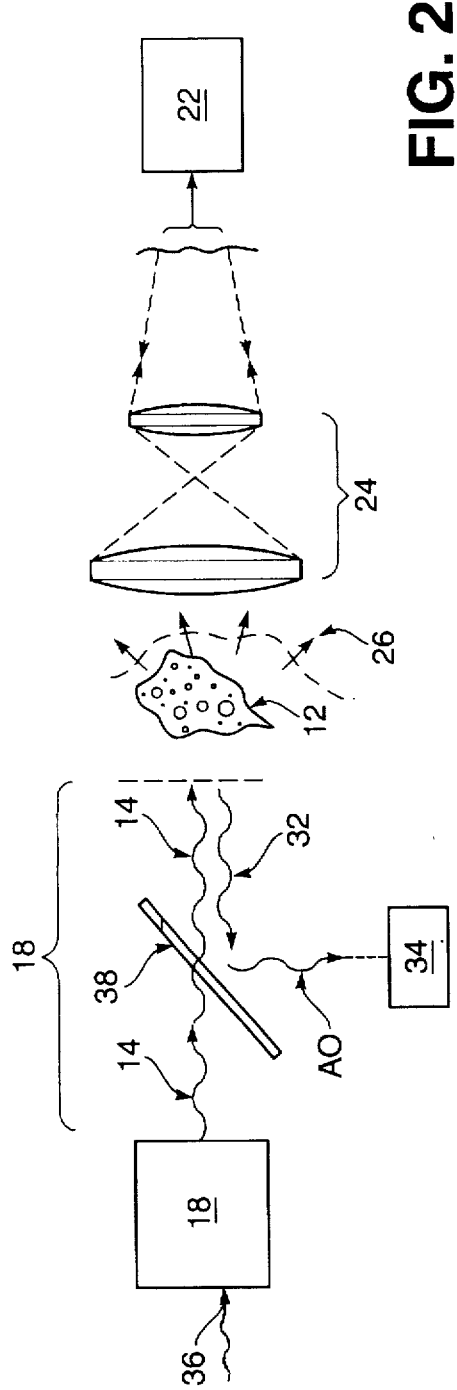
FIG. 2 is a partial optical diagram depicting one modification of the system as diagrammed in FIG. 1.

As diagrammed in FIG. 2, the light beam 14 originating from the coherent light source 16 through beam control 18 according to one embodiment is transmitted through a beam splitter 38 which deflects some of the retroflected light 32 toward the image detector 34. The light beam 14, incident on the tissue target 12 is scattered over a relatively wide angle shown as scattered light 26 which is gathered and concentrated so as to collect all information therefrom as well as to decrease angular spread and increase intensity of the incident light on the phase conjugate mirror 22 for improved performance thereof. To correct for image distortions induced by light scattering from tissue target 12 over a wide angle, especially in view of associated backscattering, all of the light 26 scattered into the half space to the right of the tissue target 12 as viewed in FIG. 2 is conjugated. Collimating optics 24 hereinbefore referred to gathers all this light and naturally concentrates it upon directing it onto the necessarily finite reception aperture of the phase conjugate mirror 22. The optics 24 also collimates this light, that is, greatly reduces the range of angles of incidence of the light incident on the phase conjugate mirror 22, which aids in maintaining a uniform mirror response.

Figure 3:
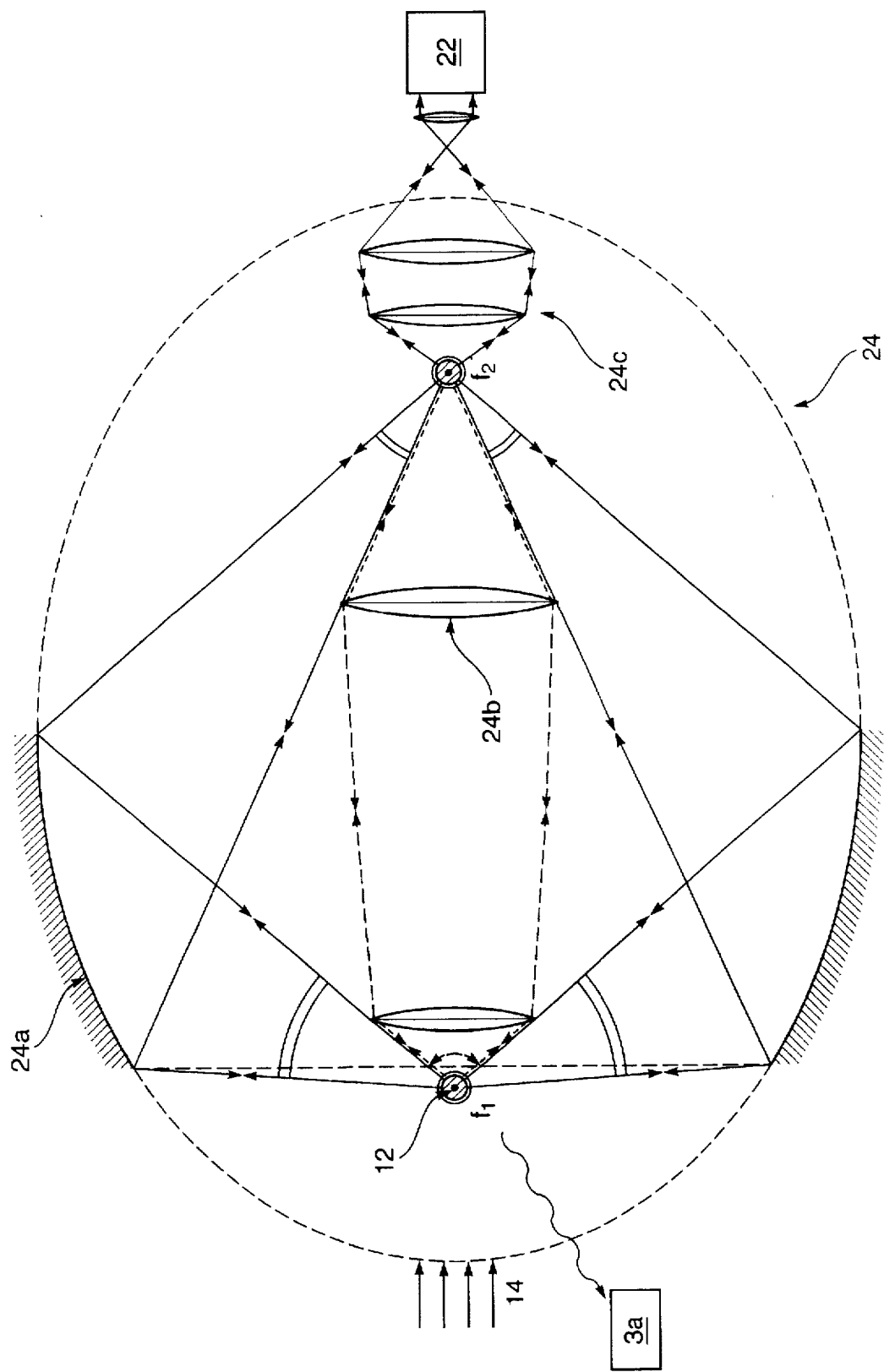
FIG. 3 is an optical diagram depicting in greater detail the collimating optics diagrammed in FIG. 1.

According to the embodiment of the collimating optics 24 as depicted in FIG. 3, all light is shown emitted from around one focus point $f_1$ in the target 12. Such point $f_1$ is the focus of an ellipsoid of revolution of a mirror segment 24a from which all light will converge after one reflection to a second focus point $f_2$. Light emitted from the tissue target 12, contained in a small region around focus point $f_1$, will pass through a small region around focus point $f_2$, as is generally known in the art of geometrical optics. Thus, one can use mirror segment 24a to gather the more widely scattered light 26 around second focus point $f_2$. The less widely scattered light is intercepted by a smaller collimator 24b that also directs it to focus point $f_2$. Light that is still somewhat widely scattered, is then further collimated and concentrated onto the phase conjugate mirror 22 by another set of collimating optics 24c to the right of focus point $f_2$. The reflectivity (Rc) of the phase conjugate mirror 22 is greater than unity to cancel the losses in the collimating optics 24a, 24b and 24c so that the reflectivity of the system formed by the collimating optics and the phase conjugate mirror is unity.

Operation of the coherent light source 16 is either continuous or selectively controlled by pulsation control 37, as diagrammed in FIG. 1, at a rate which is related to the scattering properties of the biological tissues of target 12 to be imaged and the response time of the phase conjugate mirror 22 so as to obtain a steady state duration long enough for imaging to occur at detector 34. The source 16 is accordingly turned on by control 37 during intermittent time intervals so that a series of images are produced that appear to be continuous. Further, intermittent exposure of the tissue target 12 to the light of source 16 will thereby be minimized to avoid tissue damage despite the increased intensity of such illuminating light.

Based on the foregoing description of the imaging system 10, the coherent light source 16 meets several conditions. First, the light 36 emitted by source 16 has a frequency or wavelength in the red or near infrared region so that scattering of light predominates over the weak absorption in the biological tissue of target 12 to be examined. Such wavelength region of light 36 is such that absorption is at a minimum (650–1200 nm, or preferably 800–900 nm). Second, the light beam 14 is wide enough to illuminate the entire target 12 to be examined, and yet has sufficient intensity to allow the phase conjugate mirror 22 to operate without damaging the target tissue.

Also, the coherence length/time of the illumination from source 16 exceeds a minimum value determined by the appreciable spread in time of passage of the illumination through the target 12 due to multiple scattering and reflections between the target 12 and the phase conjugate mirror 22.

Figure 4:
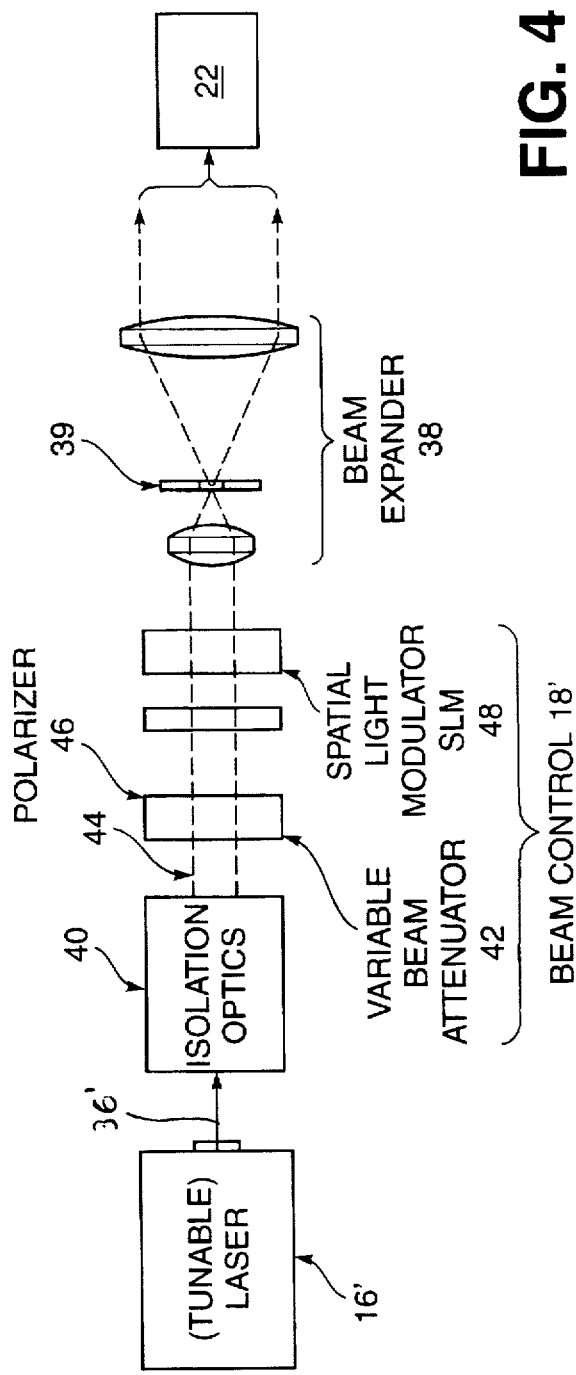
FIG. 4 is a block diagram depicting in greater detail certain components of the system depicted in FIG. 1.

Various laser devices may be utilized to construct a suitable source 16 in the arrangement of the imaging system 10 as hereinbefore described. According to the embodiment depicted in FIG. 4, the coherent light source is in the form of a frequency tunable laser 16' from which a narrow output beam 36' is emitted. Such laser source 16' is therefore associated with a beam control 18' having an expander lens component 38 so as to illuminate the entire target tissue sample of target 12. The intensity of the narrow output beam 36' is high enough so that when expanded by beam expander 38 it is still intense enough to allow operation of phase conjugate mirror 22. Such output beam 36' from laser 16' is passed through isolation optics 40 of the beam control 18' to a variable beam attenuator 42 along beam path 44 to control beam intensity. Specific polarization of the beam electromagnetic field is then ensured by a polarization filter 46. Also, a spatial light modulator 48 is placed in the light path 44 between polarizer 46 and the beam expander 38 to clean up undesirable deviations in phase or amplitude. A spatial filter 39 placed within the beam expander 38 can also clean up the beam 44. According to yet other embodiments, the high power and narrow emission beam laser 16' and beam expander 38 may be replaced by an array of individually low power and wide angular emission diode lasers that emit a physically wide beam. To ensure single mode emission and high coherence, such an array may be coupled to an external phase conjugate mirror, which is already present for tissue target imaging purposes.

As hereinbefore indicated, different types of phase conjugate mirror arrangements may be utilized, involving for example: a four wave mixing process in a suitably thick slab of a non-linear medium; a quantum well structure or superlattice of alternating layers having a thickness in the order of 10 nm; use of an optically addressed spatial light modulator for phase conjugation; or use of integrated optics to record incident wavefront intensities, compute phase differences and radiate the phase conjugate wavefront to selectively control reflection magnitude and phase, wavefront polarization and time delay of the conjugate reflection.

Figure 5:
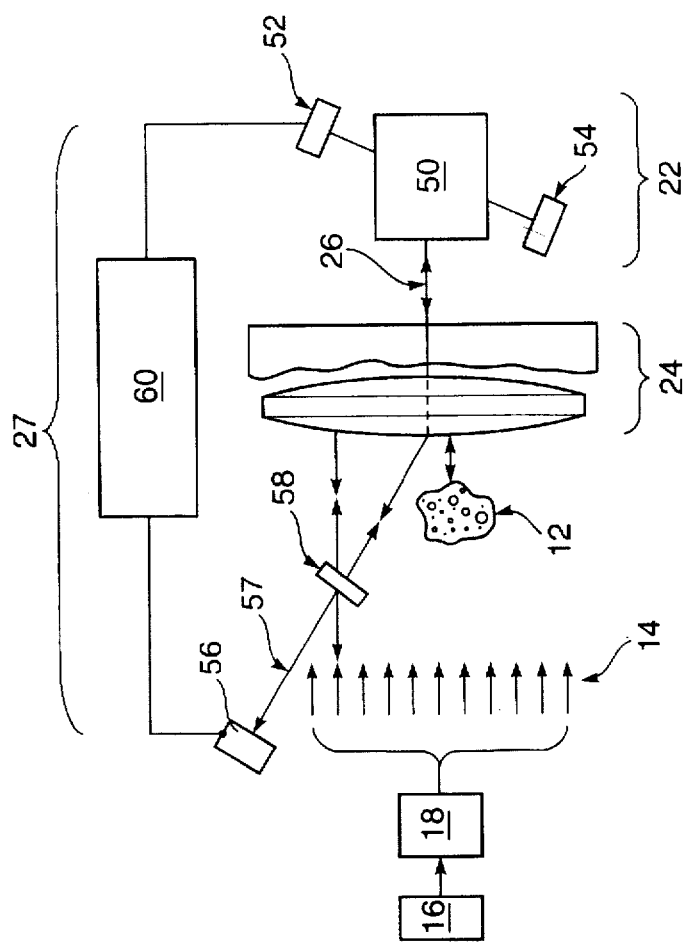
FIG. 5 is a block diagram depicting in greater detail certain components of the system diagrammed in FIG. 1.

FIG. 5 diagrams by way of example a phase conjugate mirror 22 having a non-linear (Kerr) medium 50 within which a degenerate four wave mixing process occurs by virtue of pump beams 52 and 54 of the same frequency and coherent with beam 26 as a probe fed at room temperature to medium 50 from light diverted from coherent beam 36 by means of beam splitters and directed by mirrors to the medium 50. The intensities of the pump beams 52 and 54 are equal and are varied by a regulating device 60 of the reflectivity monitor and control 27 having a monitoring photodetector 56 in a position outside of the illuminating light beam 14 from the coherent light source 16. The photodetector 56 measures the intensity (Ir) of light 57 received from a small transparent dielectric plate 58 positioned within the beam 14 laterally of the target 12 and closer to the source 16. The light 57 consists of direct reflection by plate 58 of light 14 and light returned through plate 58 from multiple reflections between plate 58, the collimating optics 24 and mirror 22. Such reflection monitoring measurement by the photodetector 56 is fed to the regulating device 60 through which the intensity (Ir) of the pump beams 52 and 54 are adjusted until intensity of 57 vanishes, at which point the conjugate reflection equals unity (Rc=1).

Based on the foregoing description of the present invention, the use of phase conjugation to image weakly absorbing features in human biological tissue as the illuminated scattering medium, of target 12, has been demonstrated. Also, suppression of multiple scattering effects therein by the phase conjugate mirror 22 for biomedical imaging purposes is achieved, despite the effects of target illumination absorption, by substantially maintaining unity of reflectivity (Rc=1) without correction for absorption induced distortion as the basis for imaging by the phase conjugate mirror 22. Other constraints imposed on the phase conjugate mirror 22 include a complete reversal of any arbitrary state of electric field polarization of the incident radiation 26 upon retroreflection into beam 20.

The phase conjugate mirror 22 is spaced from the illumination scattering target 12 by a sufficient amount to avoid an incident electric field with evanescent modes, and is furthermore capable of conjugating incident fields of arbitrary polarization at room temperature with a response time that is shorter than natural changes in the target tissue, of approximately 20 msec. for human body tissue. Also, the phase conjugate mirror 22 operating in the red or near infrared region will conjugate the light with an intensity too weak to damage the biological tissue of target 12.

Obviously, other modifications and variations of the present invention may be possible in light of the foregoing teachings. It is therefore to be understood that within the scope of the appended claims the invention may be practiced otherwise than as specifically described.

What is claimed is:

1. In a system for imaging a target disposed between a source of coherent light and phase conjugation means through which reversal of radiation is effected, said target being translucent to the coherent light with little absorption and through which multiple scattering predominates over absorption of the coherent light before emergence therefrom of said radiation applied to the phase conjugation means, an image detector, optical means for regulating imaging by said image detector in response to the radiation retroreflected from the target following said reversal thereof by the phase conjugation means and control means for maintaining reflectivity of the radiation from the phase conjugation means substantially at unity.

2. The system as defined in claim 1 wherein said target is biological tissue.

3. The system as defined in claim 2 wherein said optical means includes beam control means for limiting intensity of the coherent light illuminating the target to a level avoiding damage thereto and means for establishing a predetermined angular scattering dimension of incident wavefront of the radiation applied to the phase conjugation means to maximize said imaging of the biological tissue by the image detector.

4. The system as defined in claim 3 including pulsation control means connected to the source of the coherent light for limiting said illuminating of the target to periods of time of greater duration than response of the phase conjugation means and interaction with the target.

5. The system as defined in claim 1 including pulsation control means connected to the source of the coherent light for limiting said illuminating of the target to periods of time of greater duration than response of the phase conjugation means to emission of the coherent light from said source and interaction with the target.

6. The system as defined in claim 5 wherein said optical means includes beam control means for limiting intensity of the coherent light illuminating the target to a level avoiding damage to the target.

7. The system as defined in claim 6 wherein said optical means further includes means for establishing a predetermined angular scattering dimension of the radiation applied to the phase conjugation means to maximize said imaging of the target by the image detector.

8. The system as defined in claim 6 including collimating means for gathering the illuminating light scattered by the target and concentration thereof into the radiation applied to the phase conjugation means.

9. In a system for imaging biological tissue disposed between a source of coherent light and phase conjugation means through which incident wavefront reversal of radiation is effected, said biological tissue causing multiple scattering of the coherent light which predominates over weak absorption thereof by the biological tissue before emergence of said radiation therefrom applied to the phase conjugation means, an image detector receiving the radiation resulting from said incident wavefront reversal following illumination of the biological tissue by the coherent light and control means for maintaining reflectivity of the radiation received by the image detector from the phase conjugation means substantially at unity.

10. The system as defined in claim 9 including beam control means for limiting intensity of the coherent light illuminating the biological tissue to a level avoiding damage thereto.

11. The system as defined in claim 10 including means for establishing a predetermined angular scattering dimension of the incident wavefront of the radiation applied to the phase conjugation means to maximize said imaging of the biological tissue by the radiation received at the image detector.

12. In a system for imaging biological tissue disposed between a source of coherent light and phase conjugation means through which incident wavefront reversal of radiation is effected, said biological tissue causing multiple scattering of the coherent light which predominates over weak absorption thereof by the biological tissue before emergence of said radiation therefrom applied to the phase conjugation means, an image detector receiving the radiation resulting from said incident wavefront reversal following illumination of the biological tissue by the coherent light and means for establishing a predetermined angular scattering dimension of the incident wavefront of the radiation applied to the phase conjugation means to maximize said imaging of the biological tissue by the radiation received at the image detector.

* * * * *